United States Patent [19]

Strege

[11] 4,310,706
[45] Jan. 12, 1982

[54] IMIDAZOLE CATALYSTS FOR HYDROXYALKYLATION OF PHENOLS OR THIOPHENOLS

[75] Inventor: Paul E. Strege, Midland, Mich.

[73] Assignee: The Dow Chemical Company, Midland, Mich.

[21] Appl. No.: 179,130

[22] Filed: Aug. 18, 1980

[51] Int. Cl.$^3$ .................. C07C 41/03; C07C 41/16
[52] U.S. Cl. ............................. 568/648; 568/45; 568/55; 568/608; 568/644
[58] Field of Search ............ 568/648, 608, 55, 45, 568/644

[56] References Cited

U.S. PATENT DOCUMENTS 2,448,767  9/1948  Carlson ..................... 568/648 X

*Primary Examiner*—Bernard Helfin
*Attorney, Agent, or Firm*—Douglas N. Deline

[57] ABSTRACT

Hydroxyalkylphenyl ether or thioether compounds are prepared by reaction of cyclic organic carbonate compounds with phenols or thiophenols in the presence of an imidazole catalyst.

7 Claims, No Drawings

IMIDAZOLE CATALYSTS FOR HYDROXYALKYLATION OF PHENOLS OR THIOPHENOLS

BACKGROUND OF THE INVENTION

The present invention relates to a process for the preparation of hydroxyalkylphenyl ether or thioether compounds. More particularly, the present invention is concerned with an improved catalyst for use in the preparation of such compounds by the reaction of cyclic organic carbonate compounds with phenols and thiophenols.

Carlson disclosed in U.S. Pat. No. 2,448,767 a method of hydroxyethylation wherein ethylene carbonate or ethylene sulfite was reacted with certain organic compounds including phenols and alcohols. The reaction could be carried out in the presence or in the absence of a suitable solvent, and in the presence or in the absence of a suitable catalyst. Catalysts that were disclosed included an acid (concentrated sulfuric acid or an alkyl ester of sulfuric acid), a base (alkali carbonates), or the alkali salt of a phenol. The preferred catalyst was an alkali carbonate or alkali salt of a phenol. U.S. Pat. No. 3,283,030 disclosed use of potassium carbonate as a basic catalyst in the reaction of ethylene carbonate with certain substituted phenols.

Alkali metal hydrides disclosed by U.S. Pat. No. 2,987,555 and alkali metal hydroxides disclosed by U.S. Pat. No. 2,967,892 have also been found to be effective catalysts for hydroxyalkylation reactions of ethylene carbonate with phenols and chloromethylethylene carbonate with phenols respectively.

One disadvantage associated with prior art processes using acidic or basic catalysts has been the occurrence of secondary reactions between the hydroxyalkylphenyl ether product and the carbonate reactant forming quantities of undesirable side-products.

SUMMARY OF THE INVENTION

This invention comprises an improved process for the hydroxyalkylation of phenols or thiophenols providing high yields with good selectivity. In particular the invention comprises the use of imidazole and derivatives thereof as reaction catalysts for the reaction of phenols or thiophenols and cyclic organic carbonate compounds. Despite the fact that such compounds are generally classified as bases it has been found possible, utilizing the invented process, to attain reaction conditions conducive to exclusive monohydroxyalkylation of the phenol or thiophenol reactant. The hydroxyalkylphenyl ether or thioether products formed according to this invention are used as solvents and in certain coatings as well as in additional industrial applications.

DETAILED DESCRIPTION OF THE INVENTION

This invention lies in the discovery that imidazole and its derivatives act as an effective catalyst in the reaction of cyclic organic carbonate compounds with phenols or thiophenols.

Included in the invention are compounds of the formula

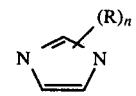

wherein R is hydrogen, phenyl, or $C_{1-4}$ alkyl, hydroxyalkyl or alkoxy and n is 4. Preferably R is hydrogen or $C_{1-4}$ alkyl or hydroxyalkyl. The most preferred catalyst is imidazole.

The amount of catalyst required to effectively catalyze the hydroxyalkylation reaction according to the present invention may vary compared to total reactant weight from about 0.1 percent to about 10.0 percent depending on the particular catalyst. It is preferred to employ the catalyst in amounts from about 0.5 percent to about 2.0 percent by weight.

The catalyst of this invention may be used by itself or in combination with other known hydroxyalkylation catalysts. The catalyst may also be employed in an unsupported state or supported by attachment to inert supportive means such as particles of alumina, silica gel, diatomaceous earths, porous glasses, zeolites, and the like. By the term zeolites is included modern synthetic resin zeolites useful as ion-exchangers as well as the well-known naturally occurring mineral formations that may be used with or without modification as ion-exchangers. Attachment of the catalyst to such materials is known, one such method having been disclosed by J. H. Clark in *J.C.S. Chem. Comm.*, 789 (1978).

The phenol- or thiophenol-containing compounds that may be hydroxyalkylated by organic carbonate compounds according to this invention are extremely varied. Carlson in U.S. Pat. No. 2,448,767 discloses a wide variety of reactive hydrogen-containing aromatic compounds including phenol, thiophenol, alkaline salts of phenol, β-naphthol, and 8-hydroxyquinoline that are capable of undergoing hydroxyalkylation with alkyl carbonate compounds. Additionally Carlson taught that all such compounds tested responded to the hydroxyalkylation reaction and it was believed all such compounds would be responsive.

Davis in U.S. Pat. No. 2,987,555 discloses an additional number of phenols that may be hydroxyalkylated by reaction with alkylene carbonates including: p,p'-biphenol, p,p'-sec-butylidene dephenol, 4,4'-isopropylidenebis(o-cresol), 4,4'-isopropylidenebis(2-phenylphenol), o-chlorophenol, o-cresol, p-propylphenol, p-bis(o-cresol) and the like.

I have found that nearly any phenol- or thiophenol-containing reactant is suitable for use according to this invention. Included are: phenol, thiophenol, and phenol or thiophenol compounds substituted with one or more hydroxy, mercapto, alkyl, aryl, alkaryl, aralkyl, halo or sulfonyl substitutents or mixtures thereof. However, Tsuruya disclosed in *J. Polymer Sci.*, Part B, 7, 709 (1969) that 2,4,6-tribromophenol, preferably forms polymers through debromination when reacted with organic carbonate compounds. This compound therefore is not considered to be suitable for use according to the present invention.

The cyclic organic carbonates used in the hydroxyalkylation reactions according to this invention may likewise be varied. In addition to ethylene carbonate, Davis in U.S. Pat. No. 2,987,555 disclosed that any cyclic alkylene carbonate having the appropriate carbonate moiety attached at adjacent positions was capable of undergoing hydroxyalkylation with phenolic compounds. Specifically mentioned carbonate compounds were propylene carbonate, 1,2- or 2,3-butylene carbonate and phenylethylene carbonate. For said disclosure I do incorporate this teaching by reference.

In addition, ethers of alkylene carbonates of the formula

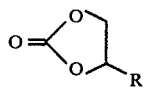

wherein R is $C_{1-20}$ alkoxy, alkoxyalkylene or (poly)alkoxyalkylene may also be used.

As previously mentioned, use of the instant catalysts has been found to lead to the exclusive formation of the monohydroxyalkylated product without concomitant formation of secondary reaction products.

The reaction may take place in the presence or absence of an inert solvent. In the preferred embodiment the cyclic carbonate reactant is a suitable solvent.

The reactants may be combined in nearly any molar ratio since some product is produced under nearly all conditions. It is preferred however, to combine the reactants in a stoichiometric ration thereby eliminating the need to remove excess reactants from the finished product in a subsequent purification step.

The reaction may be carried out in any vessel suitably designed to contain the reactants and products and be unreactive under the conditions of the invention. Representative of suitable reaction vessels are those made of glass, stainless steel or other unreactive material.

The reaction may be run in the practice of this invention at any suitable temperature from about 100° C. to about 210° C. Faster reaction rates are observed at higher temperatures but decomposition of reactants and products is likely to occur at the higher temperatures. The optimum temperature for particular reactants allowing fast reaction rates, but minimizing decomposition side-products may be easily determined according to ordinary techniques of experimentation. The preferred operating temperature for most phenolic and carbonate reactants is from about 150° C. to about 170° C. Heating the reaction vessel to the operating temperature may conveniently be occasioned by any usual means such as a heat lamp, heating mantle, oil bath, etc.

The time for the reaction to proceed to substantial completion will vary depending on various factors such as the particular phenol- or thiophenol-containing reactant, cyclic organic carbonate reactant, and temperature selected. Generally about two hours to about five hours is sufficient. The evolution of carbon dioxide is a convenient indicator of the progress of the reaction.

The reaction may be run either accompanied by mechanical or magnetic stirring or without stirring. To avoid liquid entrapment during the evolution of carbon dioxide it is also advantageous to employ a condenser according to well-known techniques in the art.

The product, a corresponding hydroxyalkyl ether or thioether derivative may be easily recovered from the reaction mixture, for example, by distillation if a liquid, or by recrystallization if a solid.

While the invention has been described as useful in a batch process reaction, it may be utilized equally advantageously in a continuous reaction process.

SPECIFIC EMBODIMENTS OF THE INVENTION

Having described the invention the following examples are given merely as illustrative of the present invention and are not to be considered as limiting.

EXAMPLE 1

Ethylene carbonate (45 g, 0.51 mole), phenol (47.1 g, 0.5 mole) and imidazole (0.5 g, reagent grade) were placed in a 250 ml glass round-bottomed flask equipped with a condenser and gas bubbler. Agitation was provided with a magnetic stirrer. The mixture was heated to 160° C.±2° C. in an oil bath. After the time indicated in Table I, the reaction vessel was removed from the oil bath and purified by distillation. The product was identified as 2-phenoxyethanol. Results are provided in Table I.

EXAMPLE 2

The conditions of Example 1 were repeated utilizing as catalysts imidazole derivatives and other organic bases. The results are contained in Table I for comparison purposes.

TABLE I

| Compound | Reaction Time (hrs.) | Percent Completion |
|---|---|---|
| Imidazole | 2 | 91 |
| 2-Methylimidazole | 2 | 97 |
| N-(2'-hydroxyethyl)-2-methylimidazole | 3 | 97 |
| Piperidine | 3 | 40 |
| Morpholine | 3 | 8 |
| Triethylamine | 3 | 94 |

It may be seen that 2-methylimidazoline and N-(2'-hydroxyethyl)-2-methylimidazole provided substantially similar results as imidazole. By contrast other cyclic amines such as piperidine and morpholine failed to demonstrate similar catalytic activity. Triethylamine was found to effectively catalyze the reaction, however, a significant amount of undesirable by-product formation was also observed. Similar by-products were not observed utilizing imidazole or its derivatives.

What is claimed is:

1. In the method of hydroxyalkylation wherein phenol- or thiophenol-containing compounds are reacted with cyclic organic carbonate compounds, selected from the group consisting or ethylene carbonate, propylene carbonate, 1,2- or 2,3-butylene carbonate, phenylethylene carbonate, and ethers of alkylene carbonates of the formula

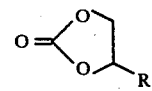

wherein R is $C_{1-20}$ alkoxy, alkoxyalkylene or (poly)alkoxyalkylene, in the presence of a catalyst followed by recovery of the hydroxyalkylaryl ether formed, the improvement wherein the catalyst is of the formula

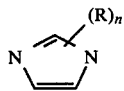

wherein R is hydrogen, phenyl, or a $C_{1-4}$ alkyl, hydroxyalkyl or alkoxy radical and n is 4.

2. The process of claim 1 wherein the catalyst is imidazole.

3. The process of claim 1 wherein the phenol- or thiophenol-containing compound and organic carbonate compound are combined in substantially stoichiometric quantity.

4. The process of claim 1 wherein the carbonate compound is ethylene carbonate.

5. The process of claim 1 wherein the reaction is carried out at a temperature from about 100° C. to about 210° C.

6. The process of claim 1 wherein the quantity of catalyst present based on total reactant weight is from about 0.1 percent to about 10 percent.

7. The process of claim 1 wherein the phenol- or thiophenol-containing compound is phenol.

* * * * *